United States Patent
Lee

(10) Patent No.: US 9,597,356 B2
(45) Date of Patent: *Mar. 21, 2017

(54) METHOD FOR TREATING CANCERS WITH DENDRITIC KILLER CELLS AND PHARMACEUTICAL COMPOSITION COMPRISING THE SAME

(71) Applicant: FULLHOPE BIOMEDICAL CO., LTD, New Taipei (TW)

(72) Inventor: Jan Mou Lee, Taipei (TW)

(73) Assignee: FULLHOPE BIOMEDICAL CO., LTD, New Taipei (TW)

(*) Notice: Subject to any disclaimer, the term of this patent is extended or adjusted under 35 U.S.C. 154(b) by 0 days.

This patent is subject to a terminal disclaimer.

(21) Appl. No.: 14/925,545

(22) Filed: Oct. 28, 2015

(65) Prior Publication Data

US 2016/0045548 A1 Feb. 18, 2016

Related U.S. Application Data

(63) Continuation-in-part of application No. 13/918,736, filed on Jun. 14, 2013, now abandoned.

(30) Foreign Application Priority Data

Jul. 5, 2012 (TW) .............................. 101124291 A

(51) Int. Cl.

| C12N 5/00 | (2006.01) |
|---|---|
| C12N 5/02 | (2006.01) |
| A61K 35/15 | (2015.01) |
| C12N 5/0784 | (2010.01) |
| C12N 5/0783 | (2010.01) |
| A61K 35/12 | (2015.01) |
| A61K 39/00 | (2006.01) |

(52) U.S. Cl.
CPC ............ *A61K 35/15* (2013.01); *C12N 5/0639* (2013.01); *C12N 5/0646* (2013.01); *A61K 2035/124* (2013.01); *A61K 2039/5154* (2013.01); *C12N 2501/2312* (2013.01); *C12N 2501/2315* (2013.01)

(58) Field of Classification Search
None
See application file for complete search history.

(56) References Cited

U.S. PATENT DOCUMENTS

2014/0010794 A1* 1/2014 Lee ..................... C12N 5/0636
424/93.71

OTHER PUBLICATIONS

Himoudi et al., 2009, Canc. Res. vol. 69: 6598-606.*
Salagianni et al. "New insights into the role of NK cells in cancer immunotherapy", OncoImmunology 1:2, 205-207; Mar./Apr. 2012.
Salagianni et al. "NK Cell Adoptive Transfer Combined with Ontak-Mediated Regulatory T Cell Elimination Induces Effective Adaptive Antitumor Immune Responses", J. Immunol. Mar. 15, 2011;186(6):3327-35.
Evans et al. "A distinct subset of human NK cells expressing HLA-DR expand in response to IL-2 and can aid immune responses to BCG", Eur. J. Immunol. Jul. 2011;41(7): 1924-1933.
Lin et al., 2004, Ped. All. Immunol. vol. 15: 79-85.
Roncarolo et al., 1991, J. Immunol. vol. 147: 781-787.
Liu et al., 2002, Nat. Med. vol. 8: 185-189.
Burt et al., 2008, Hum. Immunol. vol. 69: 469-474.
Lazana et al., 2012, Haematologica, vol. 97: 1338-1347.
Taiwan Intellectual Property Office, "Office Action", issue on Jan. 15, 2014.
Taiwan Intellectual Property Office, "Office Action", issue on Jul. 28, 2014.
Taiwan Intellectual Property Office, "Decision to Grant a Patent", issue on Sep. 19, 2014.

* cited by examiner

*Primary Examiner* — Amy Juedes
(74) *Attorney, Agent, or Firm* — WPAT, PC; Justin King; Douglas Hosack

(57) ABSTRACT

The present invention discloses a use of dendritic killer cell population for manufacturing medication. The dendritic killer cell population is generated by culturing peripheral blood mononuclear cells with effective amounts of various cytokines for an appropriate time period, and the conserved cytokine is IL-15. Meanwhile a pharmaceutical composition comprises the above dendritic killer cell population for treating cancers is also disclosed in the present invention.

9 Claims, 12 Drawing Sheets

METHOD FOR TREATING CANCERS WITH DENDRITIC KILLER CELLS AND PHARMACEUTICAL COMPOSITION COMPRISING THE SAME

CROSS-REFERENCE TO RELATED APPLICATIONS

This Non-provisional application is a continuous-in-part application claiming priority benefit from U.S. application Ser. No. 13/918,736 and claims priority under 35 U.S.C. §119(a) on Patent Application No(s). 101124291 filed in Taiwan, Republic of China, on Jul. 5, 2012, the entire contents of which are hereby incorporated by reference.

FIELD OF THE INVENTION

The present invention relates to a method for treating cancers and pharmaceutical composition comprising the same, especially relates to a method of treating cancers with dendritic killer cell population generated after culturing by cytokines, and further, the pharmaceutical composition comprises the above dendritic killer cell population.

BACKGROUND OF THE INVENTION

Human body will recognize the extraneous matter and start a series of defending process. This defense system is named as immune system. There are many different cells such as leukocytes and lymphocyte, and different protein factors such as immunoglobulins and cytokines working coordinately to protect the body. The immune systems are traditionally divided into innate and adaptive immune systems. Innate immune system is including soluble complement system, polymorphonuclear neutrophils, macrophages and natural killer cells. Adaptive immune system is including humoral and cellular immunity. Humoral immunity as well as cellular immunity involves lymphocyte, lymphokine and immunological memory system. The long-lasting immune memory mounts quick and strong immune responses towards the same pathogen which has invaded the body.

Immune system may respond to different pathogens due to the diversity of major histocompatibility complex (MHC) molecules. The endogenous and exogenous antigens derived from pathogens, are assembled with MHC molecules on the surface of antigen-presenting cells (APC) and then presented to T cells expressing corresponding T cell receptors. MHC in the human beings can be called Human Leukocyte Antigen, HLA, which can be categorized into class I, class II, and class III. HLA class I is widely expressed on all the somatic cells but Class II distribution is restricted to macrophages, B cells and dendritic cells.

Dendritic cells (DC), which have the broadest range of antigen presentation, are professional APC, and named by the appearance of dendrites extending from the cell body. DCs reside in the periphery of body as immature DCs (imDCs). Once pathogen invades human bodies, imDCs capture pathogen-derived antigens, migrate to draining lymph nodes to become mature DCs (mDCs), and present antigens to corresponding T cells there. Therefore, dendritic cells are the starter of the pathogen-specific cellular immune responses.

Natural killer (NK) cells, a key player of innate immune system, spontaneously kill cancer cellsor virally infected cells prior to activation. Mechanisms underlying cytotoxicity of NK cells are grouped into two parts: a) interaction of cell surface tumor necrosis factor superfamily members and their receptors which leads to apoptosis of target cells, (b) release of soluble perforin and granzymes. NK cells are rich with small granules in their cytoplasm contain special proteins such as perforin and proteases known as granzymes. Upon release in close proximity to a cell slated for killing, perforin forms pores in the cell membrane of the target cell through which the granzymes and associated molecules can diffuse in, leading to destruction of target cells. Once virally infected cells or cancer cells have been killed, viral genomic content (CpG or poly I:C), cellular metabolites, and bystander cytokines such as IFN-•, IL-12 and TNF-• would further activate and augment NK cell activity in term of cytotoxicity and effector cytokine production. Therefore NK cells serve as key innate effector cells targeting to virally infected cells and cancer cells in a non-antigen specific manner while DCs in adaptive immune system trigger antigen-specific cytotoxic T cells which can further clear the infection. Patients deficient in NK cells are proved to be highly susceptible to early phases of herpes virus infection.

Interferon-producing killer dendritic cells (IKDCs), a recently identified leukocyte population in mice, express phenotypes of non-T (CD3$^-$), non-B (CD19$^-$), intermediate levels of CD11c, and high levels of B220 and NK-specific markers, including NK1.1, DX5, NKG2D and Ly49 family receptors. IKDCs functionally resemble NK cells in cytotoxicity against cancer cells and in production of abundant IFN-•. On the other hand, upon stimulation with CpG or cancer cells, IKDCs down-regulate NKG2D, up-regulate MHC II, and acquire moderate APC-like activity that activates antigen-specific T cells. Despite acquisition of APC activity after certain stimulations, IKDCs appear to belong to the NK lineage rather than DC lineage. IKDCs express NK-specific Ncr-1 transcripts (encoding NKp46) but not PU.1 that is predominantly expressed in DCs and plasmacytoid DCs. Furthermore, IKDC development parallels NK cells in their strict dependence on the IL-15 cytokine system. Therefore, the putative IKDCs are functionally and developmentally similar to NK cells. Although debates regarding tumoricidal activity and cell lineage development of IKDC were raised herein, further investigations were limited by rare abundance of IKDC in periphery. The frequency of IKDCs in a mouse spleen is below 0.01%, and is even lower in the lymph nodes. Therefore, cumbersome procedure is required for the purification of IKDCs, and the yield is low. This problem has limited the use of IKDCs in research and in application.

SUMMARY OF THE INVENTION

According to the abovementioned disadvantages of the prior art, Applicant put a lot of efforts in the past years and successfully screens out cells which have the functions of both natural killer cells and dendritic Cells. The abovementioned cells are defined as Dendritic killer cell (hereafter called DKC), also be called cytotoxic dendritic cell (cytoDC). However, it is noted that the DKC constitutes less than 0.01% of peripheral lymphocytes.

Therefore, Applicant successfully makes trace DKC of human blood increase in an amount of 200-fold to 400-fold, and further use the toxicity of DKC to kill cancer cells and treat cancers. According to the abovementioned, the present invention provides a method of treating cancers with DKC and pharmaceutical composition comprising the same. Moreover, the abovementioned DKC are generated by culturing with cytokines.

The present invention provides a method for treating cancers, and the method comprises the following steps: first, DKCs are obtained from a cancer patient. And then, a DKC population is generated by culturing DKCs. Finally, the DKC population will be delivered into the cancer patient. Preferably, the DKC population is delivered into the cancer patient through intravenous injection.

Preferably, the DKC population is generated by culturing with cytokines according to the following steps. First, a step of obtaining a peripheral blood mononuclear cell population from human blood is performed. Then, at least one of the cytokines with an effective amount is added to mix with the peripheral blood mononuclear cell population and placed for an appropriate period. Finally, the DKC population will be sorted. The abovementioned cytokines comprise IL-15. Preferably, the abovementioned cytokines further comprise IL-12.

The present invention further provides a pharmaceutical composition containing a plurality of human DKCs, wherein the DKCs are HLA-G$^-$CD14$^-$CD19$^-$CD3$^-$CD56$^+$HLA-DR$^+$.

The present invention further provides a use of DKC population for manufacturing medication. Preferably, the medication is administered to the cancer patient to inhibit cancer cells growth. Preferably, the abovementioned DKC population can form a pharmaceutical composition with a buffer.

The present invention further provides a pharmaceutical composition for treating cancers, and the pharmaceutical composition comprises an effective medical dosage of DKC population and a buffer. Preferably, the pharmaceutical composition is administered to the cancer patient to inhibit the cancer cells growth.

Preferably, the DKC population comprises surface markers of CD14$^-$HLA-G$^-$CD3$^-$CD19$^-$HLA-DR$^+$CD56$^+$.

Preferably, the buffer can be selected from a group consisting of phosphate buffer and saline solution.

Preferably, the pharmaceutical composition comprises DKC population which is generated ex vivo by culturing the DKC obtained from human blood with effective amounts of various cytokines. Preferably, the human blood is collected from a cancer patient. Preferably, the abovementioned cytokine comprises IL-15. Preferably, the abovementioned cytokine further comprises IL-12.

Preferably, the abovementioned pharmaceutical composition can be administered to a cancer patient to inhibit the cancer cells growth. Preferably, the abovementioned pharmaceutical composition is administered through injection.

The present invention further provides a method of treating a cancer in a human subject in need thereof; the method comprises to administer the abovementioned composition to the human subject.

The present invention further provides a method of making a pharmaceutical composition comprising dendritic killer cells for treating cancer, the method at least comprises the steps of:
 (a) obtaining human peripheral blood mononuclear cells;
 (b) adding IL-15 and IL-12 to make the concentration of IL-12 become 0.5~20 ng/mL, and culturing the human peripheral blood mononuclear cells for several days;
 (c) isolating the cells with the surface marker HLA-G$^-$CD14$^-$CD19$^-$CD3$^-$CD56$^+$ HLA-DR$^+$ to obtain the isolated dendritic killer cells; wherein the isolated dendritic killer cells have cytotoxicity activity and antigen-presenting activity; and
 (d) making the pharmaceutical composition comprising the isolated dendritic killer cells.

Preferably, the concentration of IL-15 is 10 ng/mL.

Preferably, the concentration of IL-15 is greater than 1 ng/mL.

Preferably, after ex vivo culture, the number of dendritic killer cells among the human peripheral blood mononuclear cells increases at least 200-fold.

Preferably, the isolated dendritic killer are capable of killing at least 50% of K562 target cancer cells, and the isolated dendritic killer are capable of presenting antigens to cytotoxic T cells to activate and proliferate at least 46.1% of cytotoxic T cells.

Preferably, the isolated dendritic killer cells are capable of killing at least 85% of K562 target cancer cells.

Preferably, between the step (a) and step (b), the method further comprises the step of:
 (a1) removing T cells and B cells in the human peripheral blood mononuclear cells.

The present invention further provides a method for treating cancers, comprising the steps of:
 (a) obtaining human peripheral blood mononuclear cells from a cancer patient;
 (b) adding IL-15 and IL-12 and culturing the human peripheral blood mononuclear cells for several days, wherein the concentration of IL-12 is 0.5~20 ng/mL;
 (c) isolating the cells with the surface marker HLA-GC$^-$D14$^-$CD19$^-$CD3$^-$CD56$^+$ HLA-DR$^+$ from the cultured human peripheral blood mononuclear cells to obtain the isolated dendritic killer cells; wherein the isolated dendritic killer cells have cytotoxicity activity and antigen-presenting activity;
 (d) making a pharmaceutical composition comprising the isolated dendritic killer cells; and
 (e) administering the pharmaceutical composition to the cancer patient.

Preferably, the concentration of IL-15 is 10 ng/mL.

Preferably, the concentration of IL-15 is greater than 1 ng/mL.

Preferably, between the step (a) and step (b), the method further comprises the step of:
 (a1) removing T cells and B cells in the human peripheral blood mononuclear cells.

The features and advantages of the present invention will be understood and illustrated in the following specification and FIGS. 1-10C.

DETAILED DESCRIPTION OF THE INVENTION

Figure 1:
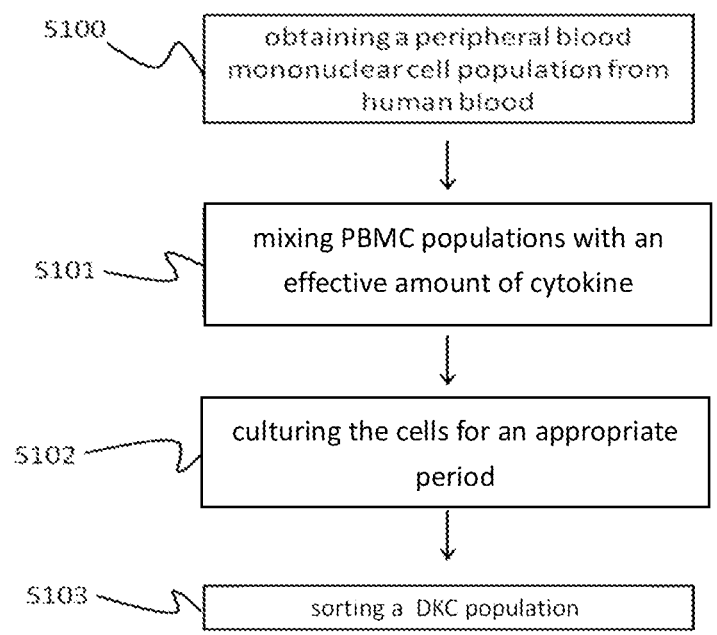
FIG. 1 is flow diagram showing a method according to an embodiment of the present invention for cultivating DKC population.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

As used herein, the term "Dendritic killer cells" or "DKC" is intended to refer to the cells with both cytotoxicity and antigen presenting cell (APC) activity.

As used herein, the term "cancer" (i.e. malignant cancer) is a group of diseases characterized by uncontrolled growth and spread of abnormal cells. From a histological standpoint there are hundreds of different cancers, which are grouped into six major categories: carcinoma, sarcoma, myeloma, leukemia, lymphoma, and mixed types. Many cancers form solid cancers, which are masses of tissue; cancers of the blood, such as leukemias, generally do not form solid cancers. (Please refer to the website of National Cancer Institute, http://www.cancer.gov/; http://training.seer.cancer.gov/disease/categories/classification.html).

On the other hand, different body tissue types (e.g. connective tissue, endothelium and mesothelium, blood and lymphoid cells, muscle, epithelial tissues, and neural et al) give rise to different cancers, both benign and malignant. Different malignant cancers, containing solid malignant cancers and non-solid malignant cancer, are relevant to different cancers. (Please refer to the website of National Cancer Institute, http://training.seer.cancer.gov/disease/categories/cancers.html).

As used herein, the term "cancer cell" means a cell that is part of a malignant cancer.

As used herein, the term "cancer antigen" means a substance produced in cancer cells and capable of inducing immune response in the host.

As used herein, the symbol "+" means that the cell surface marker expresses on the surface of the cells and has a larger expressed amount measured by flow cytometer than that of the negative control.

As used herein, the symbol "−" means that the cell surface marker does not express on the surface of the cells and has an expressed amount equal to that of the negative control.

Preferably, all abovementioned expressed amount of the cell surface markers are measured by flow cytometer, however, the present invention is not limited thereto.

As used herein, the term "Interleukin" means a group of cytokines that were first seen to be expressed by white blood cells (leukocytes). It has since been found that interleukins are produced by a wide variety of body cells. The function of the immune system depends in a large part on interleukins.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention. To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Preferably, several sorting or screening steps are performed by a flow cytometer, and a target cell population will be screened out by utilizing at least one flow cytometer to identify different surface markers of different cells. Flow cytometry allows for single cell analysis at speeds far surpassing any other single cell analysis technology in the art. This enables a statistically significant number of cells to be analyzed faster than using other alternative techniques. In a preferred embodiment, a flow cytometer is used with any suitable sample preparation robot or liquid handler that is known in the art. Furthermore, a single laser flow cytometer is used in an embodiment for the analyzing step. In another embodiment, a multi-laser flow cytometer is used for the analyzing step and the present invention is not limited thereto.

At first Applicant put a lot of efforts in the past years and successfully screens out cells which have the functions of both natural killer cells and dendritic Cells. These cells are defined as dendritic killer cell (hereafter called DKC) as mentioned above and have surface markers of HLA-G⁻CD14⁻CD19⁻CD3⁻CD56⁺HLA-DR⁺.

Prepare Dendritic Killer Cells

As abovementioned, the DKCs are identified from human peripheral blood. In the following, the method disclosed in the present invention of cultivating the DKCs from human peripheral blood for further use as DKC population in pharmaceutical composition will be illustrated through FIG. 1.

Please refer to FIG. 1, step S100 of obtaining a peripheral blood mononuclear cell population from human blood is performed at first. And then, step S101 of adding an effective amount of at least a cytokine to mix with the peripheral blood mononuclear cell population is performed. Preferably, the cytokine comprises an effective amount of Interleukin-15 (hereafter "IL-15"). The following step S102 is to place the peripheral blood mononuclear cell population for an appropriate period. Finally, a DKC population will be sorted in step S103.

Preferably, the abovementioned cytokine further comprises Interleukin-12 (hereafter "IL-12"). Preferably, the concentration of abovementioned IL-15 is greater than 1 ng/mL. Preferably, the concentration of abovementioned IL-15 is 10 ng/mL, and the concentration of IL-12 has a value between 0.5~20 ng/mL.

Preferably, the abovementioned step S100 further comprises the following steps. At first, the human blood of 40 ml is collected and the human peripheral blood mononuclear cell (hereafter "PBMC") is sorted. Then T cells and B cells are removed from the peripheral blood mononuclear cell population. The human peripheral blood mononuclear cells comprise the following five categories of cells: monocytic cells, small cells, lymphoid cells, large cells and large and granular cells. Flow cytometry can be first used to select one or more types of cells for follow steps. Preferably, the cell comprises monocytic cells or lymphoid cells or both, but the present invention is not limited thereto.

Preferably, the abovementioned appropriate period means that IL-15 and the peripheral blood mononuclear cell population are both put into a media for a period to let cell proliferation process. Preferably, the appropriate period is the seventh day after starting the abovementioned cultivating step.

EXAMPLE

In step S100', obtain 40 mL of human blood (from the first subject). Isolate peripheral blood mononuclear cell population from the human blood, and then remove B cells ($CD19^+$) and T cells ($CD3^+$) from the peripheral blood mononuclear cell population to obtain peripheral blood mononuclear cell population without $CD3^+$ cells and $CD19^+$ cells therein.

In step S101', mix these remained peripheral blood mononuclear cells ($CD3^-CD19^-$) with 10 ng/mL IL-15 and 0.5~20 ng/mL IL-12.

In step S102', culture for 7 days.

In step S103', use flow cytometry to sort the cells expressing the cell surface marker $HLA-G^-CD14^-CD19^-CD3^-CD56^+HLA-DR^+$. These sorted $HLA-G^-CD14^-CD19^-CD3^-CD56^+HLA-DR^+$ cells are the dendritic killer cells of the present invention.

Figure 2A:
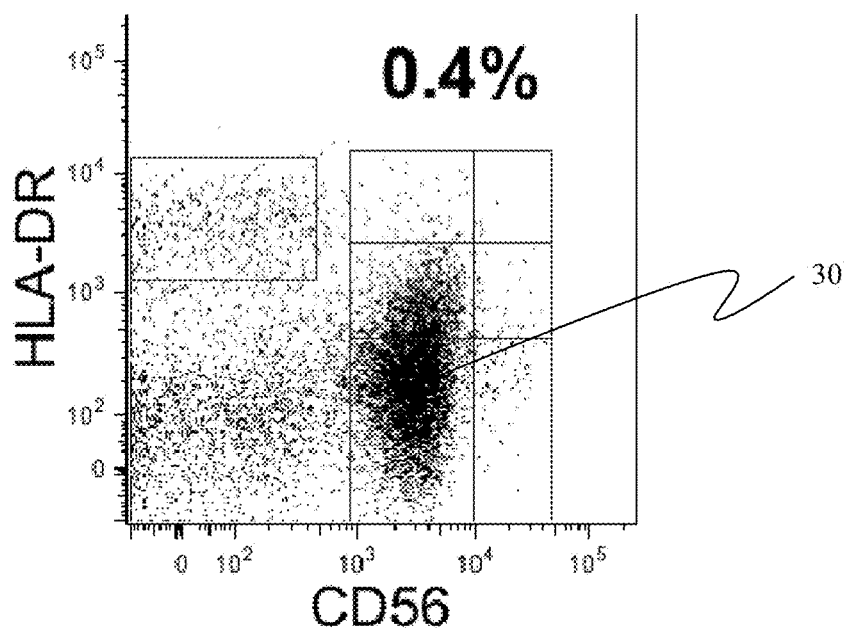
FIG. 2A to FIG. 2C are diagrams showing the results of detecting and screening cultivated DKC population by a flow cytometer.
Figure 2B:
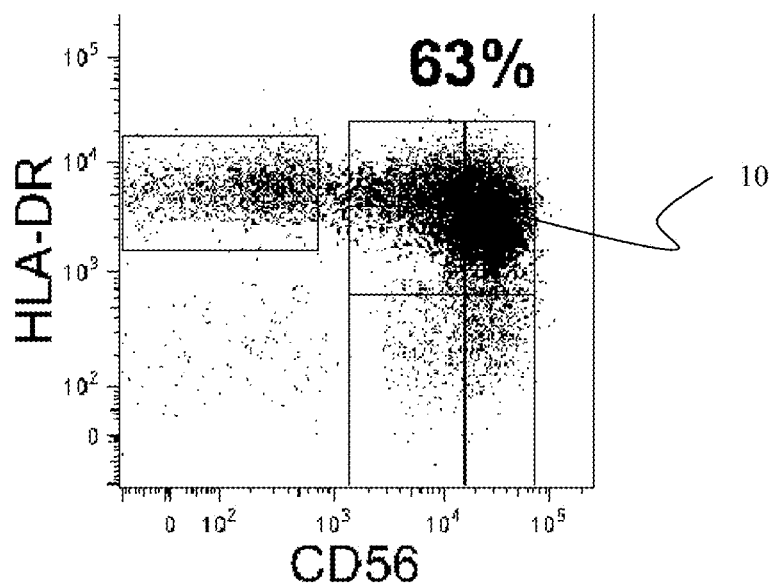
Figure 2C:
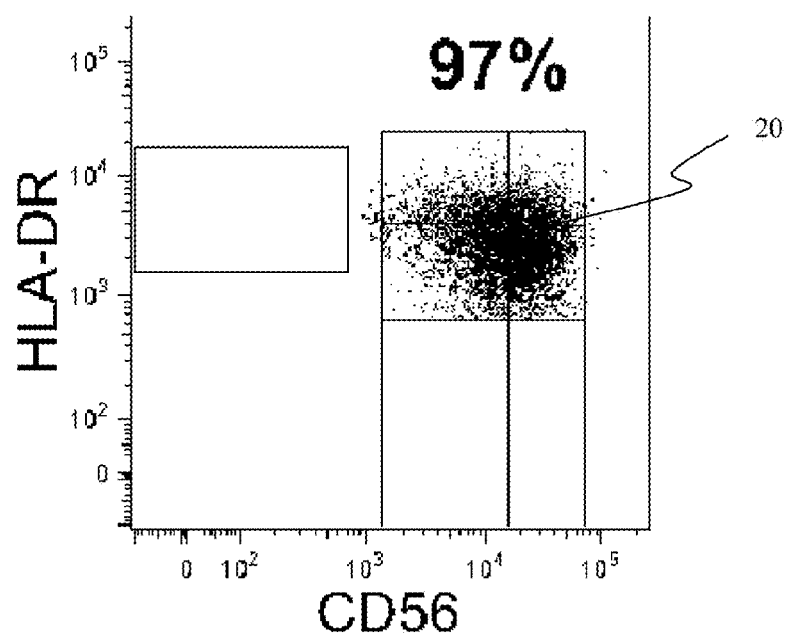

Result:

Please refer to FIG. 2; FIG. 2A illustrates the results of detecting the surface markers of CD56 and HLA-DR by a flow cytometer after removing the T cell and B cell ($CD3^-CD19^-$ PBMC) from human peripheral blood mononuclear cells and before cultivating (cells obtained from step S100'). FIG. 2B illustrates the results of detecting the surface markers of CD56 and HLA-DR by a flow cytometer at the seventh day after starting the cultivating step (cells obtained from step S102'). FIG. 2C illustrates the results of sorting DKC population (cells obtained from step S103') by a flow cytometer.

As shown in FIG. 2A, the counts of the cells which have natural killer cell surface marker ($CD56^+$) and dendritic Cell surface marker ($HLA-DR^+$) are much fewer; the proportion of this population is about 0.4%. And further, the cells 30 positioned at the central portion are natural killer cells which have the surface marker of CD56 but not HLA-DR. Please refer to FIG. 2B, after culturing with 10 ng/mL IL-15 and 0.5~20 ng/mL IL-12 for 7 days, the cells will transfer to the DKC 10 which has both natural killer cell surface marker ($CD56^+$) and dendritic cell surface marker ($HLA-DR^+$); the proportion of this DKC 10 population is about 63%. The DKCs expand the counts and further let natural killer cells transfer to DKC. Finally, FIG. 2C illustrates the sorted cells selected by flow cytometer, the DKC population 20 which has the surface marker of $HLA-G^-CD14^-CD19^-CD3^-CD56^+HLA-DR^+$.

It is noted that the abovementioned appropriate period is the preferred embodiment; however, the present invention is not limited thereto. That is, the step S103 can be performed on the fourth day after cultivating or on the tenth day after cultivating. Or, in the step S102, the cells can be cultured for 4~10 days, or the cells can be cultured for several days. Furthermore, the steps S101~S103 can be repeatedly performed after the step S103. That is, no-adherent cells will be collected again and the counts of the dendritic killer cells will be expanded to an expect value by repeating the abovementioned steps.

Preferably, the method disclosed in the present invention is processed ex vivo, wherein the human blood is collected from a cancer patient. And further, a cancer, which the cancer patient suffers from, can be selected from a group consisting of squamous cell carcinoma, lobular carcinoma in situ, liver cancer, nasopharyngeal carcinoma, lung cancer, bone cancer, pancreatic cancer, skin cancer, head and neck cancers, malignant melanoma, cervical cancer, ovarian cancer, colon cancer, anal cancer, stomach cancer, breast cancer, testicular cancer, fallopian tube cancer, endometrial cancer, cervical cancer, vaginal cancer, vulvar cancer, non-Hodgkin lymphoma, Hodgkin lymphoma, esophageal cancer, thyroid cancer, adrenal cancer, cancers of mesothelial and soft tissue, urethra cancer, cancer of penis, prostate cancer, acute leukemia, chronic leukemia, lymphomas, bladder cancer, ureteral cancer, renal cell carcinoma, urothelial carcinoma, cancer of central nervous system, primary central nervous system lymphoma, glioma, pituitary cancer, Kaposi's sarcoma, squamous cell cancer and their metastasis.

According to abovementioned, the DKC population 20 sorted from cultivating trace amount of DKC in human blood increase in an amount of 200-fold to 400-fold. Therefore, the cultivating DKC population can be administered to the cancer patient as medication to inhibit cancer cells growth. The DKC population 20 is further used to manufacture medication for treating cancers, that is, the DKC population 20 can form a pharmaceutical composition with buffer to effectively apply for cancer. Preferably, the abovementioned concentration for DKC population is $10^6$ cells/mL.

Preferably, the present invention further provides a pharmaceutical composition for treating cancer, and the pharmaceutical composition further comprises an effective medical dosage of DKC population generated by culturing with cytokines and a buffer. Preferably, the DKC population comprises the surface markers of $CD14^-HLA-G^-CD3^-CD19^-HLA-DR^+CD56^+$.

Preferably, the abovementioned DKC population is generated ex vivo by culturing the DKC obtained from peripheral blood of the cancer patient and the pharmaceutical composition is administered to a cancer patient. That is, the DKC took from the cancer patient is manufactured to the pharmaceutical composition through cultivating, and administered back to the cancer patient to inhibit cancer cells growth as medication.

Preferably, the pharmaceutical composition is transferred through injection, but the present invention is not limited thereto.

Cytotoxicity Activity of Dendritic Killer Cells

Experiment:

In order to prove the DKC population can be used for manufacturing medication and the abovementioned medication is used for treating cancers, Applicant reacts the cultivating DKC population 20 with target cell (K562) 40 and measures the cancer cell death by a flow cytometer. Cell morphology is observed by phase contrast microscopy.

Figure 3A:
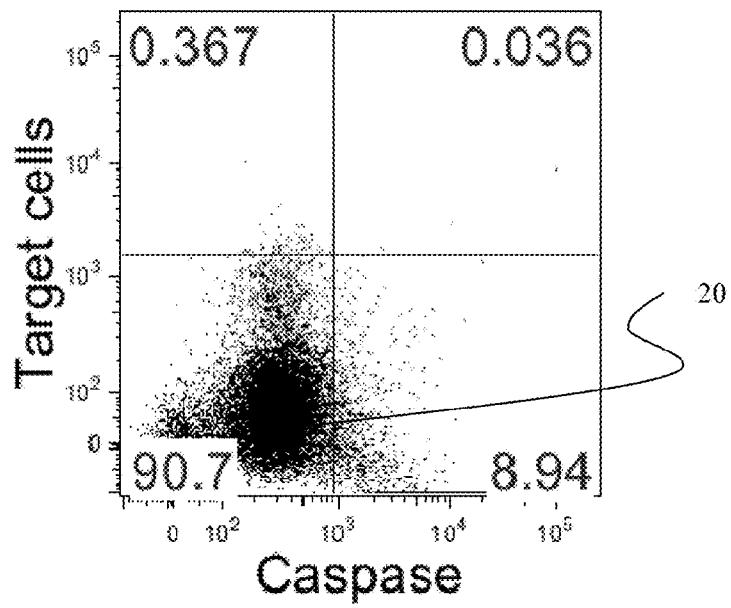
FIG. 3A to FIG. 3C are diagrams showing the results of detecting cell survival by a flow cytometer after reacting DKC population with cancer cells.
Figure 3B:
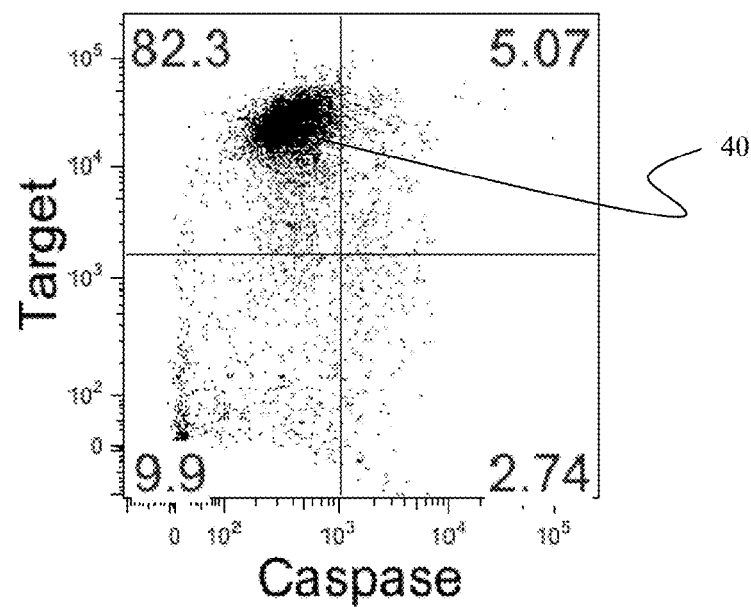
Figure 3C:
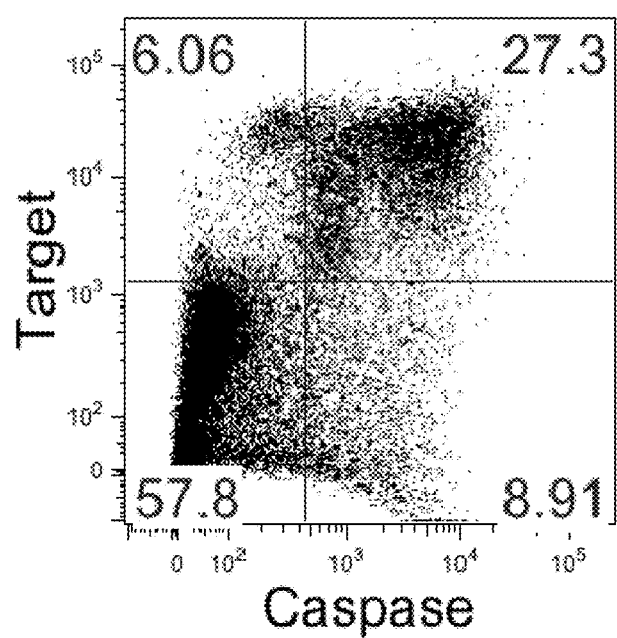

Result:

As shown in FIG. 3A to FIG. 3C, the vertical axis represents the sizes of the cells and the transverse axis represents the content of Caspase 6 in the cells. It is noted that Caspase 6 is an important protease in apoptosis so that the cell is dead or dying if Caspase 6 of the cell is dyed. That is, the killing efficiency of the DKC can be detected by detecting the content of Caspase 6 in the target cells.

Please continue referring to FIG. 3A to FIG. 3C, each of the figures is divided into four blocks: the upper portion represents the cancer cells, the lower portion represents the DKC, the left portion represents the living cells and the right portion represents the dead cells. Preferably, the target cells are K562 cells. As shown in the figures, FIG. 3A shows the abovementioned cultivating DKC 20. FIG. 3B shows the cancer cell (K562) 40 before reacting with any other cells, therefore, all cancer cells distribute at the upper left portion and no dyed Caspase 6 existed meaning the cancer cells are all living cells.

Please refer to FIG. 3C, FIG. 3C shows the result of cultivating DKC population with target cancer cells (K562) for 40 min. After reacting the cancer cells (K562) with the DKC population, the cells distributed at the upper portion apparently shift to right showing about 85% of cells are dyed with caspase 6. That is, a lot of the cancer cells (K562) decease. However, most DKC population at the lower portion survived showing a great toxicity of DKC to cancer cells.

Figure 4A:
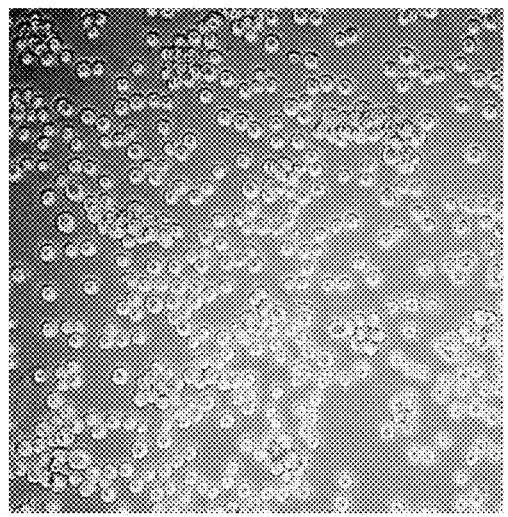
FIG. 4A to FIG. 4B are diagrams showing the results before and after addition of cancer cells into the pharmaceutical composition according to an embodiment of the present invention.
Figure 4B:
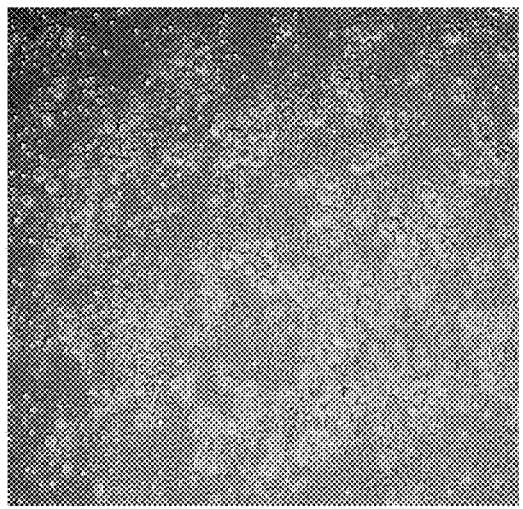

Please refer to FIG. 4A to FIG. 4B, they show the results of cell growth for original cancer cells and cancer cells cultivating with DKC population for 40 min. As shown in FIG. 4A, the cancer cells (K562) grow perfectly in media before adding DKC population. However, a lot of the cancer cells (K562) decease after reacting with the DKC as shown in FIG. 4B.

Figure 5:
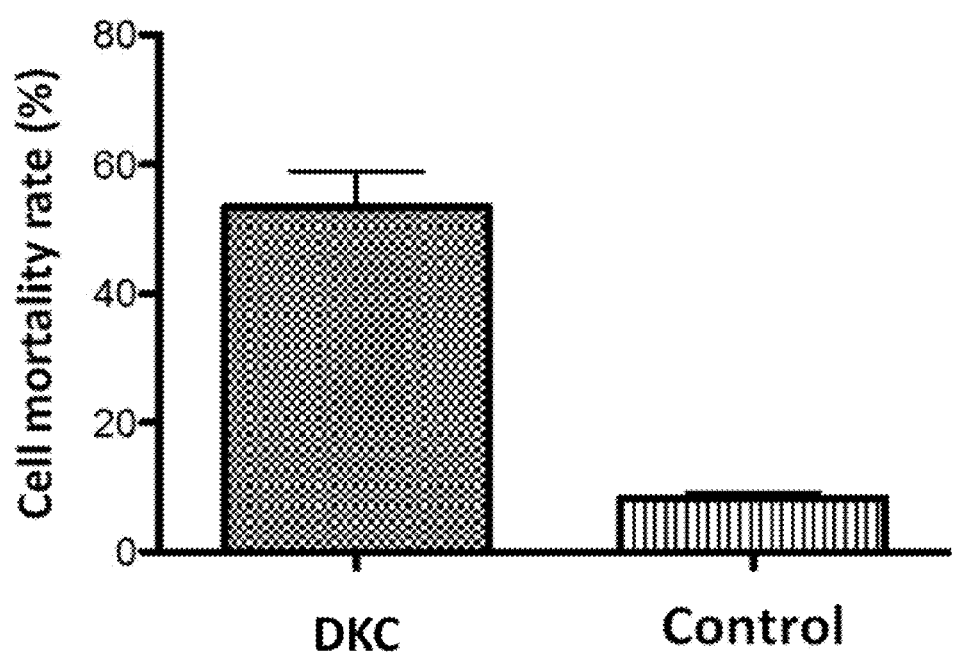
FIG. 5 is a diagram showing the cell mortality rate of control and pharmaceutical composition according to an embodiment of the present invention.

Please refer to FIG. 5, it shows the cell mortality rate of control and pharmaceutical composition with cancer cell concentration of $10^6$ cells/mL. As shown in the figure, the cancer cells decreases over half after adding DKC population, that is, over half of the cancer cells are killed by DKC population. However, the control (media only) decreases less than 10%.

Experiment:

Co-culture of "IL-15+IL-12-cultured DKC population 20" with cancer cells obtained from a patient (e.g. ovarian cancer cells). Cell morphology is observed by phase contrast microscopy.

Figure 6A:
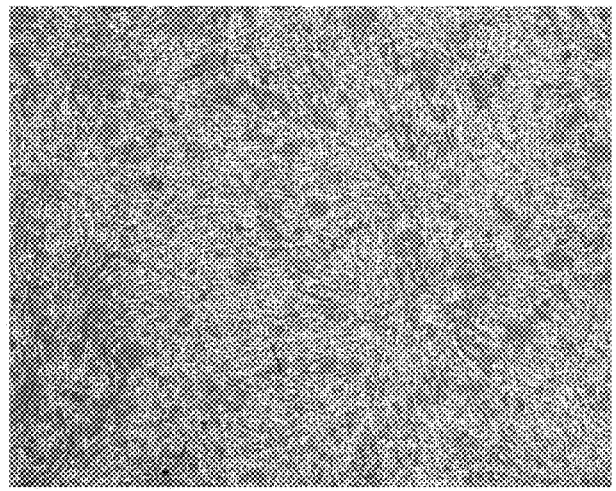
FIG. 6A to FIG. 6B are diagrams showing the results before and after addition of ovarian cancer cells into the pharmaceutical composition according to an embodiment of the present invention.
Figure 6B:
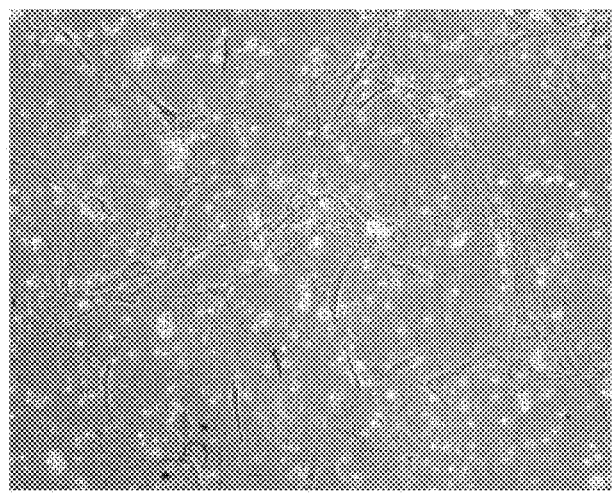

Result:

Please refer to FIG. 6A to FIG. 6B, which are the results before and after addition of $10^6$ cells/mL DKC populations into ovarian cancer cells obtained from a cancer patient. As shown in FIG. 6A, the ovarian cancer cells obtained from patient surgery were put in media and grew normally before react with DKC. And then, after reacting with DKC population cultivating from the peripheral blood of the patient with ovarian cancer for 40 min, a lot of the cancer cells decreases as shown in FIG. 6B.

In order to prove the cell population used in the present invention was DKC, that is, containing the cytotoxicity and antigen presenting function. The abovementioned DKC shows cytotoxicity by killing cancer cells, and the below experiment proves the existence of antigen presenting function. Please refer to FIG. 7 to FIG. 8.

Antigen-Presenting Activity of Dendritic Killer Cells

Applicant cultures DKC prepared from the first subject with the allogeneic T cell in peripheral blood mononuclear cells of a second subject. And then, the T cell activation and proliferation of the second subject will be measured by a flow cytometer.

Experiment:

In step S201', obtain "IL-15+IL-12 cultured dendritic killer cells" from above-mentioned step S103'.

In step S202', prepare the CFSE-labeled PBMC (i.e., CFSE-labeled responder PBMC, or referred to "responder cells"), wherein the PBMC are obtained from another healthy individual (the second subject).

In step S203', culture CFSE-labeled responder PBMC for 72 hours (hereafter called Control Group). In addition, co-culture of CFSE-labeled responder PBMC with "IL-15+IL-12 cultured dendritic killer cells" for 72 hours following the ratio of two to one (hereafter called Experiment Group).

In step S204', use flow cytometry to analyze CFSE-labeled responder PBMC which process cell proliferation and secrete interferon gamma (hereafter called "IFN-γ"). Please note that only T cells in the PBMC will be activated by the dendritic killer cells and then proliferate and secrete IFN-γ.

Result:

Please refer to FIG. 7; a mixed leukocyte reaction is utilized by culturing the DKC sorted from PBMC of the first subject with CFSE-labeled T cells of the second subject (step S203'). And then, the DKC of the first subject will activate the T cells of the second subject. Therefore, the activation and proliferation of T cells of the second subject can represent alto-stimulatory APC activity of DKC of the first subject. The abovementioned CFSE is a dye for quantifying the degree of cell proliferation. After each cell proliferation, the fluorescence intensity of CFSE will decrease. However, when CFSE labeling is performed optimally, approximately 7-8 cell divisions can be identified before the CFSE fluorescence is too low to be distinguished above the autofluorescence background. Thus CFSE represents an extremely valuable fluorescent dye for immunological studies, allowing lymphocyte proliferation, migration and positioning to be simultaneously monitored.

Figure 7A:
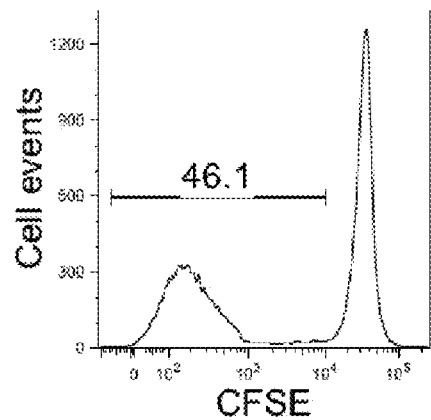
FIG. 7A to FIG. 7B are diagrams showing the antigen presenting results of cultured DKC detecting by a flow cytometer.
Figure 7B:
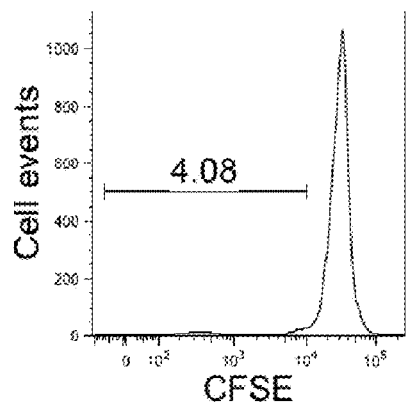

Please refer to FIG. 7A; it shows a result of reacting the DKC cultivating from the first subject and T cell labeled with CFSE from the second subject (the result of Experiment Group). As shown in the figures, the vertical axis represents the content of the cells and the transverse axis represents the fluorescence intensity of CFSE within the cells. Please continue referring to FIG. 7A; 46.1% T cell of the second subject have been activated by the DKC of the first subject to processing cell proliferation. FIG. 7B is negative control (the result of Control Group). In negative control, T cell of the second subject is lonely put inside s medium, and only 4.08% of T cell has been activated and proliferate. That is, the DKC identified and screened by the present invention actually has the antigen presenting cell activity.

Figure 8A:
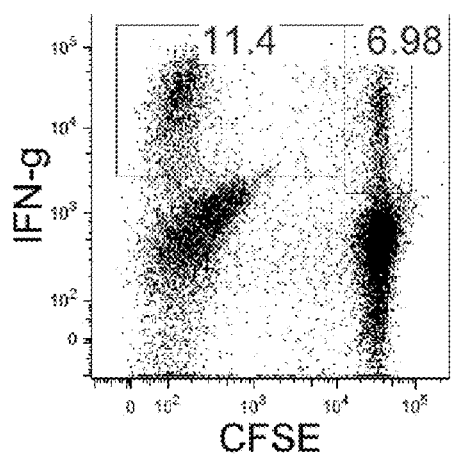
FIG. 8A to FIG. 8B are diagrams showing the results of Interferon γ presenting by activated T cells detecting by a flow cytometer.
Figure 8B:
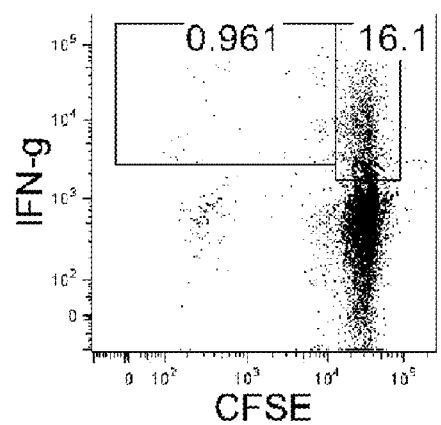

Please refer to FIG. 8; it shows a result of interferon-γ (hereafter "IFN-γ") in T cells after reaction from FIG. 7. As shown in FIG. 8A (the result of Experiment Group), most T cells activated by DKC population contain IFN-γ (distribute at the upper left portion; the proportion of the T cells containing IFN-γ is about 11.4%) and no detectable IFN-γ in T cells T cell of the second subject lonely put inside medium as shown in FIG. 8B (the result of Control Group; the proportion of the T cells containing IFN-γ is about 0.961%).

The Effect of IL-15 and IL-12 on Dendritic Killer Cells Preparation

Experiment:

In Step 1, obtain human peripheral blood mononuclear cells (PBMC) from a healthy individual, and then remove B cells and T cells from the peripheral blood mononuclear cell population to obtain peripheral blood mononuclear cell population without any $CD3^+$ cells or $CD19^+$ cells therein.

The CD3⁻CD19⁻ PBMC are divided into three groups: "Fresh cell" group, "IL-15" group, and "IL-15+IL-12" group.

In step 2, use flow cytometry to analysis the cell populations of "Fresh cell" group.

In step 3, seed 1×10⁶/ml CD3⁻CD19⁻ human peripheral blood mononuclear cells in a plate and then culture the cells with 20 ng/ml (Preferably, 10~40 ng/ml) IL-15 for 10 (Preferably, 7-10) days ("IL-15" group). Seed 1×10⁶/ml CD3⁻CD19⁻ human peripheral blood mononuclear cells in another plate and then culture the cells with 20 ng/ml (Preferably, 10~40 ng/ml) IL-15 and 4 ng/ml (Preferably, 0.5~20 ng/ml) IL-12 for 10 (Preferably, 7-10) days ("IL-15+IL-12" group).

In step 4, calculate the cell number in "IL-15" group and "IL-15+IL-12" group. Use flow cytometry to analysis the cell populations of "IL-15" group and "IL-15+IL-12" group.

Result:

There are only $3.15×10^7$ cells in the "IL-15" group after culturing; there are $5×10^7$ cells in the "IL-15+IL-12" group after culturing.

Figure 9A:
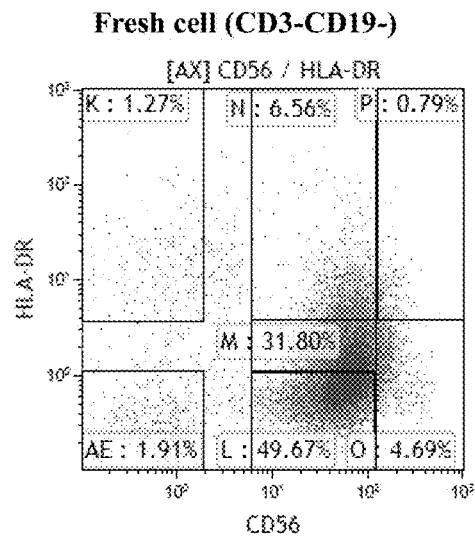
FIGS. 9A, 9B, and 9C are diagrams showing the cell populations of "Fresh cell" group, "IL-15" group, and "IL-15+IL-12" group respectively.
Figure 9B:
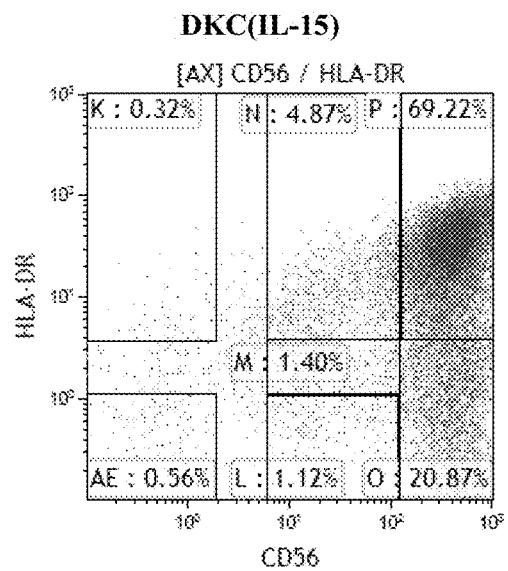
Figure 9C:
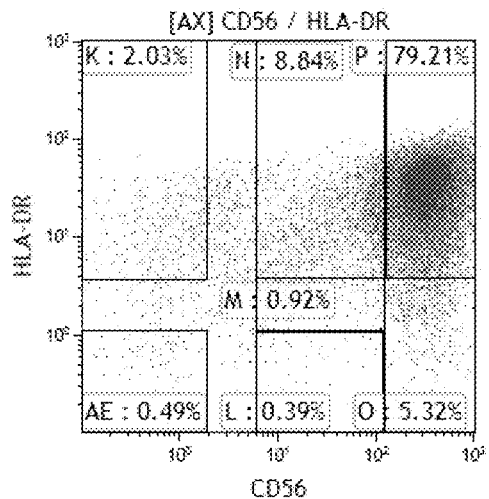

Please Refer to FIG. 9A to 9C. FIG. 9A shows the cell populations of "Fresh cell" group; FIG. 9B shows the cell populations of "IL-15" group; FIG. 9C shows the cell populations of "IL-15+IL-12" group. In the Fresh cell group (FIG. 9A), the proportion of the cells with natural killer cell surface marker (CD56⁺) and dendritic Cell surface marker (HLA-DR⁺) is 0.79%. After culture with IL-15 (FIG. 9B), the proportion of the cells with natural killer cell surface marker (CD56⁺) and dendritic Cell surface marker (HLA-DR⁺) is much higher and becomes 69.22%. On the other hand, after culture with IL-15 and IL-12 (FIG. 9C), the proportion of the cells with natural killer cell surface marker (CD56⁺) and dendritic Cell surface marker (HLA-DR⁺) is even higher and becomes 79.21%. Therefore, comparing to the result shown in IL-15 group, the combination of IL-12 and IL-15 enhances the number of dendritic killer cells by 82%. $[(5×10^7×79.21\%–3.15×10^7×69.22\%)/(3.15×10^7×69.22\%)=82\%]$ The Effect of IL-15 and IL-12 on the Antigen-Presenting Activity of Dendritic Killer Cells Experiment:

In step 5 (after above-mentioned step 4), by using flow cytometry, sort the cells expressing the cell surface marker HLA-G⁻CD14⁻CD19⁻CD3⁻CD56⁻HLA-DR⁺ from "IL-15" group, and "IL-15+IL-12" group respectively to obtain dendritic killer cells therein.

In step 6, prepare the CFSE-labeled PBMC (i.e., CFSE-labeled responder PBMC, or referred to "responder cells") from another healthy individual.

In step 7, culture CFSE-labeled responder PBMC for 72 hours (hereafter called "Responder cell alone" group). In addition, co-culture of dendritic killer cells obtained from the "IL-15" group with CFSE-labeled responder PBMC following the ratio of two to one for 72 hours (hereafter called "IL-15 cultured DKC and responder cell" group). On the other hand, co-culture of dendritic killer cells obtained from the "IL-15+IL-12" group with CFSE-labeled responder PBMC following the ratio of two to one for 72 hours (hereafter called "IL-15+IL-12 cultured DKC and responder cell" group).

In step 8, harvest total cell from "Responder cell alone" group, "IL-15 cultured DKC and responder cell" group, and "IL-15+IL-12 cultured DKC and responder cell" group respectively.

In step 9, analyze CFSE-labeled responder PBMC in the three groups which process cell proliferation respectively via flow cytometry.

Figure 10A:
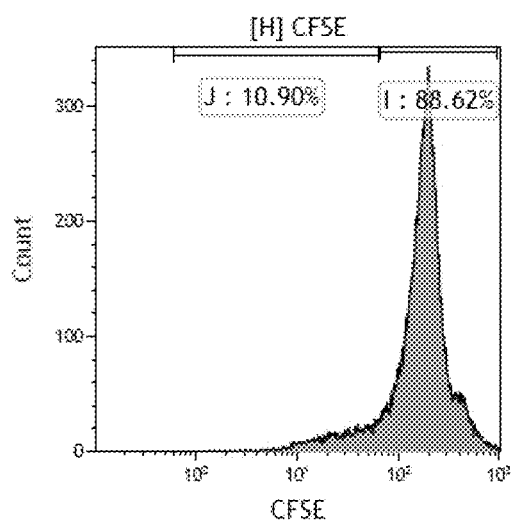
FIGS. 10A, 10B, and 10C are diagrams showing the antigen-presenting activity of dendritic killer cells in "Responder cell alone" group, "IL-15 cultured DKC and responder cell" group, and "IL-15+IL-12 cultured DKC and responder cell" group respectively.
Figure 10B:
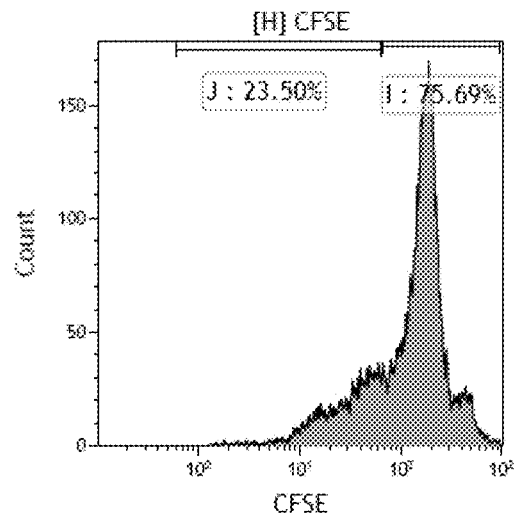
Figure 10C:
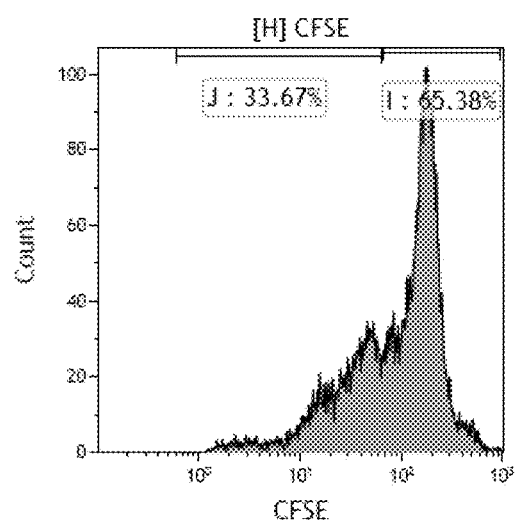

Result:

Please Refer to FIG. 10A to 10C. FIG. 10A shows the antigen-presenting activity of dendritic killer cells from "Responder cell alone" group; FIG. 10B shows the antigen-presenting activity of dendritic killer cells from "IL-15 cultured DKC and responder cell" group; FIG. 10C shows the antigen-presenting activity of dendritic killer cells from the "IL-15+IL-12 cultured DKC and responder cell" group. Responder cells expressed 10.9% of proliferative responses in the group of "Responder cell alone" (FIG. 10A). On the other hand, dendritic killer cells from the "IL-15" group activates responder cells to proliferate by 23.50% (FIG. 10B). Dendritic killer cells from the "IL-15+IL-12" group activates responder cells to proliferate by 33.67% (FIG. 10C). Therefore, comparing to the result shown in Responder cell alone group, IL-15 enhances the antigen-presenting activity of DKC by 116%. [(23.5–10.9)/10.9=116%]. Besides, comparing to the result shown in IL-15 group, the combination of IL-12 and IL-15 enhances the antigen-presenting activity of DKC by 43%. [(33.67–23.5)/23.5=43%].

In this embodiment, that IL-15+IL-12 cultured DKC has higher antigen-presenting activity and is capable of activating more allogeneic CD8⁺ T cells have been proven. This information and the related mechanism indicate that after the IL-15+IL-12 cultured DKCs present a cancer antigen, these DKCs presenting the specific cancer antigen will activate more autologous cancer antigen-specific CD8⁺ T cells. Therefore, IL-15+IL-12 cultured DKCs in the present invention can be used to prepare an efficient pharmaceutical composition for treating cancer.

To sum up, DKC is a cell with function from both natural killer cell and dendritic cell. Although DKC plays an important role in immunoreactions, the content of the DKC in the human body is very rare. The trace DKC of the human blood can be expanded from 200-fold to 400-fold by the cultivating, screening and sorting technique disclosed in the present invention. Moreover, the DKC used in the present invention is medication for treating cancer. That is, the pharmaceutical composition for treating cancer comprises a dendritic killer cell population and a buffer and the pharmaceutical composition can be administered back to the same patient to treat cancer.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

What is claimed is:

1. A method of making a pharmaceutical composition comprising dendritic killer cells for treating cancer, the method at least comprises the steps of:
   (a) obtaining human peripheral blood mononuclear cells;
   (b) adding IL-15 and IL-12 to make the concentration of IL-12 become 0.5-20 ng/mL, and culturing the human peripheral blood mononuclear cells;
   (c) isolating HLA-G⁻CD14⁻CD19⁻CD3⁻CD56⁺HLA-DR⁺ dendritic killer cells from the cultured human peripheral blood mononuclear cells; wherein the HLA-G⁻CD14⁻CD19⁻CD3⁻CD56⁺HLA-DR⁺ dendritic killer cells have cytotoxicity activity and antigen-presenting activity; and (d) making the pharmaceutical composition comprising the isolated dendritic killer cells.

2. The method of making the pharmaceutical composition according to claim 1, wherein in the step (b), the concentration of IL-15 is 10 ng/mL.

3. The method of making the pharmaceutical composition according to claim 1, wherein in the step (b), the concentration of IL-15 is greater than 1 ng/mL.

4. The method of making the pharmaceutical composition according to claim 1, wherein after ex vivo culture, the number of HLA-G$^-$CD14$^-$CD19$^-$CD3$^-$CD56$^+$HLA-DR$^+$ dendritic killer cells among the human peripheral blood mononuclear cells increases at least 200-fold.

5. The method of making the pharmaceutical composition according to claim 1, wherein between the step (a) and step (b), the method further comprises the step of:
(a1) removing T cells and B cells in the human peripheral blood mononuclear cells.

6. A method for treating cancers, comprising the steps of:
(a) obtaining human peripheral blood mononuclear cells from a cancer patient;
(b) adding IL-15 and IL-12 and culturing the human peripheral blood mononuclear cells, wherein the concentration of IL-12 is 0.5-20 ng/mL;
(c) isolating HLA-G$^-$CD14$^-$CD19$^-$CD3$^-$CD56$^+$HLA-DR$^+$ dendritic killer cells from the cultured human peripheral blood mononuclear cells; wherein the HLA-G$^-$CD14$^-$CD19$^-$CD3$^-$CD56$^+$HLA-DR$^+$ dendritic killer cells have cytotoxicity activity and antigen-presenting activity;
(d) making a pharmaceutical composition comprising the isolated dendritic killer cells; and
(e) administering the pharmaceutical composition to the cancer patient.

7. The method for treating cancers according to claim 6, wherein in the step (b), the concentration of IL-15 is 10 ng/mL.

8. The method for treating cancers according to claim 6, wherein in the step (b), the concentration of IL-15 is greater than 1 ng/mL.

9. The method for treating cancers according to claim 6, wherein between the step (a) and step (b), the method further comprises the step of:
(a1) removing T cells and B cells in the human peripheral blood mononuclear cells.

\* \* \* \* \*

UNITED STATES PATENT AND TRADEMARK OFFICE
CERTIFICATE OF CORRECTION

PATENT NO. : 9,597,356 B2
APPLICATION NO. : 14/925545
DATED : March 21, 2017
INVENTOR(S) : Lee et al.

It is certified that error appears in the above-identified patent and that said Letters Patent is hereby corrected as shown below:

On the Title Page

Item (12) "Lee" should read:
-- Lee, et al. --.

Item (72) Inventor is corrected to read:
-- Jan Mou Lee, Taipei (TW);
Nan-Shih Liao, Taipei City (TW) --.

Signed and Sealed this
Fifth Day of March, 2019

Andrei Iancu
*Director of the United States Patent and Trademark Office*